(12) United States Patent
Libman et al.

(10) Patent No.: US 6,524,561 B2
(45) Date of Patent: *Feb. 25, 2003

(54) COMPOSITION INCLUDING SEA BUCKTHORN OIL EXTRACT AND ANTIOXIDANT AND/OR A UV FILTER

(75) Inventors: Michael Libman, Southampton, PA (US); Vadim Zolotarsky, Springfield, NJ (US)

(73) Assignee: Altai Cosmetics, Ltd., Springfield, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/735,075

(22) Filed: Dec. 12, 2000

(65) Prior Publication Data

US 2001/0000466 A1 Apr. 26, 2001

Related U.S. Application Data

(63) Continuation of application No. 09/268,139, filed on Mar. 12, 1999, now Pat. No. 6,187,297.

(51) Int. Cl.⁷ .............. A61K 7/42; A61K 7/44; A61K 7/06; A61K 47/00; A61K 7/00
(52) U.S. Cl. .......... 424/59; 424/60; 424/70.9; 424/401; 424/439; 514/844; 514/904
(58) Field of Search ............... 424/401, 59, 60, 424/70.9, 439, 195.1; 514/844, 904

(56) References Cited

U.S. PATENT DOCUMENTS 5,578,307 A * 11/1996 Wunderlich et al. ... 424/195.01

FOREIGN PATENT DOCUMENTS

| DE | 4431394 C1 | * | 2/1996 |
| JP | 363145210 A | * | 6/1988 |
| JP | 402108613 A | * | 4/1990 |
| JP | 09208484 | * | 8/1997 |
| RO | 62981 | * | 11/1977 |
| RO | 63707 | * | 6/1978 |
| RO | 81790 | * | 6/1983 |

OTHER PUBLICATIONS

Kharitonova et al., "Creation of new sun protection series" (Abstract), International Scientific–Practical Conference, Biologically Active Substances and New Cosmetic Products, Moscow, Nov. 26–28, 1996, 135.*

* cited by examiner

Primary Examiner—Jose' G. Dees
Assistant Examiner—Marina Lamm
(74) Attorney, Agent, or Firm—Darby & Darby

(57) ABSTRACT

A composition that includes Sea Buckthorn Oil may be used as a cosmetic product, a pharmaceutical or nutraceutical product or a food product. The composition maintains its distinctive color, due to the use of Sea Buckthorn Oil, over time, even when exposed to oxygen and/or U.V. light. The color of Sea Buckthorn Oil is maintained by adding to the composition Sea Buckthorn Oil in an amount from 0.01 to 90% by weight and an antioxidant and/or a U.V. filter in an amount from 0.001 to 20% by weight.

17 Claims, No Drawings

COMPOSITION INCLUDING SEA BUCKTHORN OIL EXTRACT AND ANTIOXIDANT AND/OR A UV FILTER

This is continuation, of application Ser. No. 09/268,139 filed Mar. 12, 1999 now U.S. Patent 6,189,297. Each of these prior applications is hereby incorporated herein by reference, in its entirety.

BACKGROUND OF THE INVENTION

1. Field of the Invention

The present invention relates to a cosmetic product, an oral or topical pharmaceutical or nutraceutical product and a food product that includes Sea Buckthorn oil extract and an antioxidant and/or a UV filter to maintain, over time, the distinctive color that Sea Buckthorn oil provides to the product.

2. Discussion of the Related Art

Oil produced from Sea Buckthorn (Hippophae rhomboides) berries has been used in cosmetic products, such as, for example, creams, shampoos and gels. Sea Buckthorn Oil is currently produced by two principal methods. First, is a cold press method where fruit pulp, with or without the kernel, is fed to a centrifuge and oil is separated from the remaining mass. The second method is by extraction with an organic solvent, such as Freon or hexane. Extraction may also be with an inorganic matter, such as carbon dioxide. The oil produced is sometimes referred to as Sea Buckthorn Oil, Sea Buckthorn Oil Concentrate or Sea Buckthorn Oil Extract. The oil produced by any of these or other methods will hereinafter be referred to as Sea Buckthorn Oil. The terms Sea Buckthorn Oil, Sea Buckthorn Extract and Sea Buckthorn Kernal Extract have been defined in the Cosmetic Toiletry and Fragrance Association (CIFA) Dictionary, the disclosure of which is hereby incorporated by reference. Sea Buckthorn oil has a distinct color that varies from orange to orange-red. But the amount of Sea Buckthorn oil used in conventional cosmetic products has been so low that the color of the cosmetic has not been altered by the Sea Buckthorn Oil (i.e., the cosmetic product typically remains white in color).

In their formulations for cosmetic, pharmaceutical, nutraceutical or food products, the present inventors have used a sufficient amount of Sea Buckthorn oil so that the color of the final product varies from yellow to orange depending upon the amount of Sea Buckthorn used. But, in use, the distinctive color that Sea Buckthorn oil provides to the product deteriorates or fades over time. The present inventors believe that the color degradation is due to exposure to oxygen and/or UV light.

SUMMARY OF THE INVENTION

Accordingly, it is an object of the present invention to provide a composition for use as a cosmetic product, a pharmaceutical or nutraceutical product or a food product that includes Sea Buckthorn oil, but does not have its distinctive color, which Sea Buckthorn oil provides, degrade over time, even when exposed to oxygen and/or U.V. light.

In a currently preferred exemplary embodiment, the color of Sea Buckthorn oil is maintained by adding Sea Buckthorn oil in an amount from 0.01 to 90% by weight and an antioxidant and/or a U.V. filter in an amount from 0.001 to 20% by weight to the composition.

DETAILED DESCRIPTION OF THE PRESENTLY PREFERRED EXEMPLARY EMBODIMENT

The present invention is directed towards a cosmetic product, such as, for example, a skin care product including cream, gel, lotion or soap, etc. The cosmetic product may also be a haircare product, such as, for example, shampoo, conditioner, styling gel, etc. The cosmetic product includes Sea Buckthorn oil in an amount from 0.01 to 20.0% by weight and an antioxidant and/or a U.V. filter is in an amount from 0.001 to 20.0% by weight. More preferably, the Sea Buckthorn oil is in an amount from 0.10 to 5.0% by weight, and the antioxidant and/or U.V. filter is in an amount from 0.010 to 5.0% by weight. Still even more preferably, the amount of Sea Buckthorn oil is from 0.5% to 2.0% by weight and the amount of antioxidant and/or U.V. filter is from 0.010 to 2.0% by weight.

A pharmaceutical or nutraceutical product, such as, for example, a topical pharmaceutical product, like a cream, ointment, lotion, gel or paste, etc. preferably contains Sea Buckthorn oil in an amount from 0.010 to 60.0% by weight and an antioxidant and/or U.V. filter in an amount from 0.0010 to 20.0% by weight. More preferably, the amount of Sea Buckthorn oil is in an amount from 0.10 to 20.0% by weight and the antioxidant and/or U.V. filter is in an amount from 0.010 to 10.0% by weight. Even more preferably, the amount of Sea Buckthorn oil is from 0.50 to 5.0% by weight and the amount of antioxidant and/or U.V. filter is from 0.1 to 5.0% by weight.

For an oral pharmaceutical or nutraceutical product, such as, for example, a syrup or a mixture, etc., the Sea Buckthorn oil is in an amount from 0.50 to 90.0% by weight and the antioxidant and/or U.V. filter is an amount from 0.01 to 10.0% by weight. More preferably, the amount of Sea Buckthorn oil is from 10.0 to 50.0% by weight and the amount of antioxidant and/or U.V. filter is in an amount from 0.05 to 5.0% by weight. Even more preferably, the amount of Sea Buckthorn oil is from 15.0 to 35.0% by weight.

For a food product, such as a juice drink or a syrup, the amount of Sea Buckthorn oil is in an amount from 0.50 to 60.0% by weight and the amount of antioxidant and/or U.V. filter is in an amount from 0.001 to 20.0% by weight. More preferably, the amount of Sea Buckthorn oil is from 10 to 50.0% by weight and the amount of antioxidant and/or U.V. filter is in an amount from 0.01 to 10.0% by weight. Even more preferably, the amount of Sea Buckthorn oil is from 10.0 to 30.0% by weight and the amount of antioxidant and/or U.V. filter is from 0.10 to 5.0% by weight.

The food product can be used in combination with the cosmetic applications of the present application. It is believed that when the syrup or oil is taken orally, the efficacy of the topical cosmetic is enhanced by providing the necessary nutrients to the skin from "the inside". This type of method of utilizing both a cosmetic and oral food product is known as an "inside-out" method.

The antioxidants that may be used in the present invention include, but are not limited to, the substances listed as "antioxidants" in the International Cosmetic Dictionary and Handbook, which is hereby incorporated by reference. For example, a natural oil containing antioxidants and some enzymes possesses antioxidant properties. Likewise, the U.V. filters that may be used in the present invention include, but are not limited to, those listed as "sunscreen agents" in the International Cosmetic Dictionary and Handbook. Additionally, zinc oxide and avobenzone may also be a U.V. filter.

The following numbered Examples illustrate representative gels or creams compositions embodying the present invention.

EXAMPLE 1

A gel, containing 5.0% (Wt.) Sea Buckthorn oil and no antioxidants and/or U.V. filters, was kept in the dark at room temperature. The distinctive orange color started to deteriorate after one (1) month. After two (2) months the color changed to light yellow-green.

EXAMPLE 2

A gel, containing 5.0% (Wt.) Sea Buckthorn oil and 0.5% (Wt.) Tocopherol as an antioxidant, was kept in the dark at room temperature. The gel retained its original orange color over a 2 year period.

EXAMPLE 3

A cream containing 0.5% (Wt.) Sea Buckthorn oil and no antioxidants and/or U.V. filters was tested in the dark at elevated temperature (50° C.) for three (3) months. The cream color changed from golden-yellow to light yellow in two (2) weeks. In the two (2) following months the color changed to white.

EXAMPLE 4

A cream containing 0.5% (Wt.) Sea Buckthorn oil and 0.1% (Wt.) Tocopherol as an antioxidant, was tested in the dark at elevated temperature (50° C.) for three (3) months. There was no change in color over a three (3) month period.

EXAMPLE 5

Two creams both containing 0.5% (Wt.) Sea Buckthorn oil and 0.1% (Wt.) Tocopherol, one of them with 0.05% (Wt.) Benzophenone-4 as a sunscreen, were simultaneously exposed to direct sunlight. The cream sample that did not have a sunscreen changed color from golden yellow to white after one (1) month of exposure to sunlight. The other cream sample, which includes the sunscreen, retained its original golden yellow color over the same period of time and under the same exposure conditions.

Having described the presently preferred exemplary embodiment of a composition including Sea Buckthorn oil and antioxidant and/or a U.V. filter (e.g., sunscreen) of the present invention, it is believed that other modifications, variations and changes will be suggested to those skilled in the art in view of the teachings set forth herein. It is, therefore, to be understood that all such modifications, variations, and changes are believed to fall within the scope of the present invention as defined by the appended claims.

What is claimed is:

1. A cosmetic product having a yellow to orange color, the cosmetic product comprising:

Sea Buckthorn Oil in an amount from 0.01 to 20.00% by weight, which is sufficient to provide the product with its yellow to orange color; and an antioxidant in the amount of from 0.1 to 5.0% by weight, which is sufficient to prevent the yellow to orange color of the product from degrading over time.

2. The cosmetic product according to claim 1, wherein the amount of said Sea Buckthorn Oil ranges from 0.10 to 5.0% by weight.

3. The cosmetic product according to claim 2, wherein the amount of said Sea Buckthorn Oil ranges from 0.50 to 2.0% by weight.

4. The cosmetic product according to claim 1, wherein the amount of said antioxidant ranges from 0.1 to 2.0% weight.

5. The cosmetic product according to claim 2, wherein the amount of said antioxidant ranges from 0.1 to 2.0% weight.

6. The cosmetic product according to claim 3, wherein the amount of said antioxidant ranges from 0.1 to 2.0% weight.

7. A topical pharmaceutical or nutraceutical product having a yellow to orange color comprising:

Sea Buckthorn Oil in an amount from 0.010 to 20.00% by weight, which is sufficient to provide the product with its yellow to orange color; and an antioxidant in an amount from 0.1 to 5.0% by weight, which is sufficient to prevent the yellow to orange color of the product from degrading over time.

8. The product according to claim 7, wherein the amount of said Sea Buckthorn Oil ranges from 0.10 to 20.0% by weight.

9. The product according to claim 8, wherein the amount of said Sea Buckthorn Oil ranges from 0.50 to 5.0% by weight.

10. The cosmetic product according to claim 1, further comprising a U.V. filter in an amount from 0.001 to 20% by weight.

11. The cosmetic product according to claim 10, wherein the amount of said U.V. filter ranges from 0.010 to 5.0% by weight.

12. The cosmetic product according to claim 2, wherein the amount of said U.V. filter ranges from 0.010 to 5.0% by weight.

13. The cosmetic product according to claim 3, wherein the amount of said U.V. filter ranges from 0.010 to 5.0% by weight.

14. The product according to claim 7, comprising a U.V. filter in an amount from 0.010 to 20% by weight.

15. The product according to claim 14, wherein the amount of said U.V. filter ranges from 0.01 to 10% by weight.

16. The cosmetic product according to claim 8, wherein the amount of said U.V. filter ranges from 0.01 to 10% by weight.

17. The cosmetic product according to claim 9, wherein the amount of said U.V. filter ranges from 0.011 to 10% by weight.

* * * * *